United States Patent [19]

Burton et al.

[11] 4,199,497

[45] Apr. 22, 1980

[54] PROL A FRACTION RECOVERY METHOD AND PRODUCT

[75] Inventors: Lawrence Burton, Commack; Frank Friedman, New York, both of N.Y.

[73] Assignee: Immunology Research Foundation, Inc., Long Island, N.Y.

[21] Appl. No.: 880,545

[22] Filed: Feb. 23, 1978
(Under 37 CFR 1.47)

Related U.S. Application Data

[63] Continuation-in-part of Ser. No. 600,026, Jul. 29, 1975, Pat. No. 4,082,732.

[51] Int. Cl.² .............................................. A23J 1/06
[52] U.S. Cl. ..................... 260/112 B; 210/DIG. 23; 422/44
[58] Field of Search ....................... 260/112 R, 112 B; 23/258.5 R; 210/DIG. 23

*Primary Examiner*—Paul R. Michl
*Attorney, Agent, or Firm*—Kramer & Brufsky

[57] ABSTRACT

A process is provided for the isolation of a mammalian blood protein fraction or derivative thereof, herein termed the "Prol A" fraction. The process comprises a series of centrifugal separations of blood fractions under conditions which maintain the integrity of the desired material as it existed in vivo.

The "Prol A" fraction is a new material which constitutes another aspect of the invention. Prol A, a protein or derivative thereof, is useful as a neoplastic tissue remission and prevention agent.

5 Claims, No Drawings

PROL A FRACTION RECOVERY METHOD AND PRODUCT

CROSS-REFERENCE TO RELATED APPLICATIONS

This application is a continuation-in-part of copending application Ser. No. 600,026 filed July 29, 1975, now U.S. Pat. No. 4,082,732.

FIELD OF THE INVENTION AND PRIOR PUBLICATIONS

The present invention relates to a method for isolating a specific fraction of mammaliam blood. It relates further to the provision of a composition (Prol A) which can be administered as a tumor remission agent to tumor bearing mammals and which causes tumor tissue to undergo necrosis soon after the agent is administered. This composition also can be administered to prevent tumor formation in healthy mammals.

The inventors have published the following articles, relating to the field of this invention:
1. Annals of The New York Academy of Sciences, Vol. 100, Part II, pages 791–814 (1963)
2. Pigment Cell Biology, pages 279–299, Academic Press, 1959
3. Transactions of The New York Academy of Sciences, Ser. II, Vol. 25, pages 29–32 (Nov. 1962).

BACKGROUND OF THE INVENTION

The quest for a cure for cancer has involved the expenditure of billions of dollars for research, millions of scientist hours of effort, the construction of institutions devoted to the problem and generation of a body of literature, and yet, not even the nature of the problem, let alone its solution, has been discovered.

Approaches to the seemingly neverending search have fallen into three general categories: surgical, radiological and chemotherapeutic. Each has a modicum of success for treating certain types of tumors. Surgery, for example, can completely cure breast cancer if the operation is properly performed in the early stages of tumor growth, but will only temporarily prolong life if performed when the tumor is in advanced stages of growth. Even if breast cancer is cured by complete removal of tumor cells and the surrounding tissue, there are self-evident disadvantages to this approach.

Radiological and chemical treatment of cancer cells reduces mitotic division of cancel cells and thus reduces, if not completely inhibits the rate of tumor growth, but such treatments have several distinct and widely known disadvantages. In the first place, neither treatment is selective only to cancel cells; they damage both healthy and tumor cells. Radiological treatment is generally useful only when the tumor cells are in a relatively localized state, since any attempt to treat the body generally to control widely dispersed cancer cells would inflict great damage on the healthy cells of the host animal. Known chemotherapeutic agents such as the nitrogen mustards, because of their destructive side effects are considered a treatment of last resort to used only when other treatments have failed.

The present invention relates to a new chemotherapeutic approach to the treatment of cancer. The problems in attempting to find a chemotherapeutic cancer cure are manifold because the chemistry of the onset of cancer is as complex as life itself. Prior investigators have generally concentrated their efforts on the development of "synthetic" chemotherapeutics, i.e., extracorporeal chemicals. Massive programs, sponsored by both governmental and private agencies, have been set up to screen old and new chemicals for anti-tumor activity and tens of thousands of chemicals have been thus examined, but to date, a cancer cure has not been discovered.

SUMMARY OF THE INVENTION

The present invention have proceeded in their quest for a chemotherapeutic means to reduce or inhibit tumor growth, on several assumptions. One assumption is that mammals have within their blood one or more growth components which control cell division (mitosis) and growth, i.e., a anticancer immune defense mechanism (IDMC). A second assumption is that a balance proportion of these components leads to normal cellular mitosis and growth; whereas, an imbalance leads to malignant neoplasms, i.e., malignant tumors. The third assumption is that these growth components can be isolated from blood, without deactivating them, more easily than they could be synthesized. And the fourth assumption was that administration of such growth components to a tumor bearing mammalian host would result in reduction and/or remission of neoplasmic tissue formation, i.e., cause the host's natural IDMC to function.

The theories upon which the present invention are based are not inconsistent with immunologic theories that the immune system can defend the body from cancer, provided the system itself is not impaired. However, theoretical considerations do not cure, and the incomprehensible complexity of IDMC has until now prevented its reduction to practice. The problem is that in the process of extracting and handling biologic materials away from their in vivo environment, it is difficult to avoid the traumatic effect of the extraction process on the material itself. All steps of the extraction and handling processes had to be governed by the imperative that the extracted material had to be preserved as it existed in vivo, with as little alteration or damage as possible.

Since the materials which were sought were unknown in structure, although it could be presumed that they were polypeptides or proteins or derivatives thereof, the success of each step in following this imperative had to be determined emperically, i.e., by trial and error.

For example, if a fraction of a mouse's blood is injected into a tumor bearing mouse, and the tumor does not respond, the the blood fraction may be centrifuged to give a sediment and a supernatant, each of which is again tested on tumor bearing mice. If, again, the tumors do not respond, then perhaps the blood fraction is centrifuged at a higher speed. If, for example, the resultant sediment is injected and causes a positive response, then it is clear that centrifuging at the higher speed resulted in the separation of a tumor controlling component. Also to be considered is the question "What is in the supernatant that, before being separated from the active sediment, inhibited the tumor activity of the material in the sediment."

Proceeding in the foregoing fashion, the inventors were able to isolate three blood components or fractions, the presence in balanced proportion of which, both inhibits the formation, and causes the necrosis of neoplasmic tissue. These components are virtually nontoxic and have no apparent side effects or adverse effect on normal tissue. The toxicity is so minimal that an L.D. 50 has thus far not been obtainable.

Though the chemical structure of the useful blood components has not been illucidated, it being only known that they are proteins or polypeptides or derivatives thereof, the materials have been identified and named as follows:

1. Tumor Complement Fraction ("TCF")
   a peptide chain or derivative thereof that attacks a tumor and causes necrosis of the tumor tissue. Process for the isolation thereof is disclosed in co-pending application Ser. No 600,027 filed July 29, 1975.
2. Blocking Protein Fraction ("BPF")
   a substance that blocks the activity of TCF. Process for isolation thereof is disclosed in our co-pending application Ser. No. 600,028 filed July 29, 1975.
3. Deblocking Protein Fraction ("DPF")
   a protein or derivative thereof that neutralizes or "deblocks" BPF. Process for isolation thereof is disclosed in our copending application Ser. No. 600,026 filed July 29, 1975.

TCF, BPF and DPF must be in balance to maintain a tumor-free condition. In a normal animal, tumor growth is prevented by the presence of a greater amount of TCF than BPF, there being generally seven units of TCF for each unit of BPF. In a tumor-bearing animal, less TCF is present in the blood. By administering DPF to a tumor-bearing animal, it is theorized TCF can be freed again to do its work of killing tumor cells. If TCF is added along with DPF the necrosis of tumor tissue can be made to proceed at a more rapid rate. Thus, the essence of tumor treatment according to the principles discovered by the inventors, is to administer TCF and-/or DPF to thereby provide free TCF capable of necrosizing the tumorous tissue.

These principles can be used to cause neoplasmic growth (in test animals for experimental purposes), or to detect, destroy or prevent it. Detection of a healthy, remissive or tumorous condition is accomplished by analyzing the blood of the animal for the three main components and comparing a profile of these components with that of a healthy animal. Profiles of healthy, remissive and tumorous animals are distinctive and the comparison indicates the presence or absence of tumors. Furthermore, the profiles of cancerous animals are virtually identical irrespective of animal species.

Further studies have now found that the procedure employed to isolate DPF can be carried further to isolate an antibody, herein termed "Prol A" which exhibits anti-tumor activity.

Accordingly, it is an object of the present invention to provide a method of extracting Prol A from mammalian blood without significantly altering or modifying this fraction from its in vivo condition.

It is a further object to provide a mammalian blood component which is active as an anti-tumor agent.

SUMMARY OF THE INVENTION

The following Table shows the steps which can be employed to isolate Prol A from mammalian blood.

TABLE

| Step No. | Sediment No. | Supernatant No. | Description |
|---|---|---|---|
| | | | Non-Cancer Blood Serum |
| 1 | | | Mix and centrifuge |
| | 1 | 1 | sediment — supernatant fluid |
| 2 | | | ↓ centrifuge |
| | 2 | 2 | sediment — supernatant fluid |
| 3 | | | ↓ centrifuge |
| | 3 | 3 | sediment — supernatant fluid |
| 4 | | | ↓ centifuge |
| | 4 | 4 | sediment — supernatant fluid |
| 5 | | | ↓ ether extraction |
| | | 5 | non-aqueous phase — aqueous phase |
| 6 | | | ↓ ether extraction |
| | | 6 | non-aqueous phase — aqueous phase |
| 7 | | | ↓ (a) heat (b) centrifuge |
| | 5 | 7 | sediment — supernatant fluid |
| 8 | | | ↓ centrifuge |
| | 6 | 8 | sediment — supernatant fluid |

TABLE -continued

| Step No. | Sediment No. | Supernatant No. | Description |
|---|---|---|---|
| 9 | | | ↓ resuspend in Buffer |
| | 7 | | Suspension |
| 10 | | | ↓ Differential centrifuge |
| | 8 | 9 | sediment — supernatant fluid |
| 11 | | | ↓ centrifuge |
| | 9 | 10 | sediment (containing DPF) — supernatant fluid |
| 12 | | | ↓ ether extraction |
| | | 11 | non-aqueous phase — aqueous phase |
| 13 | | | ↓ (a) heat; (b) centrifuge |
| | 10 | 12 | sediment — supernatant fluid |
| 14 | | | ↓ centrifuge |
| | 11 | 13 | sediment (containing Prol A) — supernatant fluid |

The foregoing will be described in greater detail, each step, sediment and supernatant being identified with the reference numerals given in the table.

Non-cancer blood serum in buffer suspension is used as a starting material. The serum, which may not be pooled samples, is the non-cellular portion of whole blood separated from the cellular portion. Pooled samples cannot be employed because, it is theorized, pooling will set up an immune reaction which may deactivate desired components.

The buffer solution used in any of the following procedures where a buffer is employed is an alkaline buffer with nearly neutral pH such as 0.5 M $Na_2HPO_4$ having a pH of 7.5. About 2–6, preferably 4 parts of buffer are used for each part of serum, unless otherwise stated.

In Step 1, the serum is thoroughly mixed in a vortex mixer several minutes, e.g., for 20 minutes, at room temperature and then centrifuged for 10 minutes at 5400–10,000 g, preferably 6500 g, at room temperature.

The resultant supernatant 1 is centrifuged at 5400–10,000 g, preferably 6500 g, for 10 minutes at room temperature in Step 2, to give sediment 2 and supernatant 2. In step 3, supernatant fluid 2 is centrifuged at 23,000–48,000 g preferably 27,000 g, for 20 minutes at room temperature and the resultant supernatant fluid 3 is then centrifuged in Step 4 at high speeds, i.e., at $269-369 \times 10^3$ g, preferably at $369 \times 10^3$ g for 1 to 3 hours at 0° C. to give sediment 4 and supernatant fluid 4.

Sediment 3 is not employed in the ensuing steps; however, it should be observed to determine whether the serum sample used was derived from a tumor-bearing or healthy donor. The presence of a small amount of sediment indicates that the sample was derived from a healthy, non-tumorous donor. The presence of a small amount of sediment indicates that the sample was derived from a healthy, non-tumorous donor. The presence of a heavy sediment indicates that the donor in all probability had a tumor. In the latter case, the material would be discarded and the process would be recommenced from Step 1 with a new serum sample.

Supernatant 4 is twice extracted with anhydrous ethyl ether (Steps 5 and 6) using 5–10, preferably 10 parts of ether for each part of serum originally used, and in each case, the aqueous phase is retained.

In Step 7, the aqueous liquid from Step 6 is heated to 55° C.–50° C. for 5 to 10 minutes (on a water bath) and centrifuged at $35-42 \times 10^3$ g, preferably $40 \times 10^3$ g for 20–40 minutes at 0° c. giving sediment 5, which is discarded, and supernatant fluid 7 is clear, substantially colorless liquid.

Supernatant fluid 7 is ultracentrifuged at $1.05-2.69 \times 10^5$ g, preferably $1.05 \times 10^5$ g, at 0° C. for 20 minutes (Step 8), giving supernatant 8 (from which Prol A is isolated as hereinafter described) and sediment 6. In Step 9, sediment 6 is resuspended in 2–6, preferably 4 times the volume of buffer, based on the original volume of serum.

The number of absorbance units is determined spectrophotometrically in a Beckmann V Spectrophotometer. The absorbance at 340 nm is subtracted from the peak absorbance at 279 nm. This gives the total absorbance of the DPF per ml of isolate. An aliquot of this is diluted with near neutral buffer so that the absorbance unit content is 1 absorbance/ml of solution. This is serially diluted 50,000–100,000 fold. 0.5 ml aliquot of these dilutions are mixed with 0.5 ml of a standard BPF (105 units). This mixture after incubation is titrated for the BPF unit content. If there is a decreased BPF unit content, the units of BPF remaining are subtracted from the standard unit (BPF) content. This figure is divided by 9 since repeated tests (more than 100) have indicated that 9 units of DPF are antagonistic to 1 unit of BPF. Multiplication of this figure by the number of absorbances in one ml of BPF gives the unit content of BPF in one ml of the resultant isolate. The BPF assay is disclosed in the above-referred to application relating to Blocking Protein Fraction.

The suspension obtained in Step 9, after titration and dilution, if necessary, is differentially centrifuged in Step 10. This is accomplished by centrifugation at 2800–5400 g, preferably at 3500 g for 20 minutes at 0° C., followed by decanting of the supernatant and further centrifuging of the supernatant at $40$–$60 \times 10^3$ g, preferably 40, for 20 to 60 minutes.

Resultant supernatant 9 is ultracentrifuged (Step 11) at $264$–$369 \times 10^3$ g, preferably 369 g, for 90–180, preferably 90 minutes at 0° C. to give sediment 9, a material which contains the DPF content of the serum. This material can be stored at $-70°$ C. for future use or can be used directly in the following procedures.

Sediment 9 can be resuspended in buffer ($2$–$4 \times$ original volume of serum) and centrifuged at 1500–2800 g. preferably 2500 g for 10–40 minutes at room temperature. The resultant sediment can be resuspended in buffer ($2 \times$ original volume of serum) and centrifuged at 3500 g for 20 minutes at room temperature giving a supernatant fluid which may be stored at $-70°$ C. or directly filtered, assayed for DPF units (using the above-described procedure) and ampulated.

Returning now to supernatant fluid 8, the supernatant fluid, in Step 12, is extracted with anhydrous ethyl ether using 5–10, preferably 10 parts of ether for each part of serum originally used, and the aqueous phase is retained.

In Step 13, the aqueous liquid from Step 12 is heated to 55° C.–60° C. for 5 to 10 minutes (on a water bath) and ultracentrifuged at $1.05$–$2.69 \times 10^5$ g, preferably $1.05 \times 10^5$ g, at 0° C. for 20 minutes to eliminate any DPF (sediment 10) remaining at this stage. The resulting supernatant fluid 12 is ultracentrifuged at $264$–$369 \times 10^3$ g preferably 369 g$\times 10^3$, for 90–180, preferably 90 minutes at 0° C. to give sediment 11, material which contains the Prol A content of the serum.

Administration of DPF to tumor bearing animals at the ratio of 9 units of DPF to 1 unit of BPF in 1 ml of animal blood in conjunction with 7 units of TCF results in the onset of tumor necrosis. In C3Ht mice with indurated mammary tumors, the tumors become soft, boggy and approximately one-half their original size. Preferably, the two materials are administered by the subcutaneous and intramuscular route.

It has been found that Prol A is an antibody having anti-tumor activity. It is believed that although administration of Prol A, by itself, or TCF, by itself, are each ineffective, the conjoint administration of Prol A and TCF in a ratio of 1 part Prol A to 10 parts TCF to a tumor bearing animal initiates an immune mechanism whereby the Prol A and TCF unite at the tumor site causing lysis of the tumor within 24 hours.

What is claimed is:

1. A process for the isolation of Prol A comprising: (a) suspending blood serum in a nearly neutral buffered pH solution (b) centrifuging the resultant suspension at 5,400–10,000 g to isolate a first supernatant (c) centrifuging the first supernatant at 5400–10,000 g to give a second supernatant (d) centrifuging the second supernatant at 23,000–48,000 g to give a third supernatant (e) centrifuging the third supernatant at $269$–$369 \times 10^3$ g to give a fourth supernatant (f) extracting the fourth supernatant with ether and retaining the aqueous phase (g) heating the aqueous phase to 55° C.–60° C. and centrifuging at $35$–$42 \times 10^3$ g to give a fifth supernatant which is clear, substantially colorless liquid (h) centrifuging the fifth supernatant liquid at $1.05$–$2.69 \times 10^5$ g yielding a sixth supernatant (i) extracting the sixth supernatant with ether and retaining the aqueous phase (j) heating the aqueous phase to 55° C.–60° C. and centrifuging at $1.05$–$2.69 \times 10^5$ g to obtain a seven supernatant (k) centrifuging the seventh supernatant at $264$–$369 \times 10^3$ g yielding Prol A as the sediment.

2. The product produced by the process of claim 1.

3. The process of claim 1 wherein the centrifuging of step (j) is conducted at $1.05 \times 10^5$ g.

4. The process of claim 1 wherein the centrifuging of step (k) is conducted at $369 \times 10^3$ g.

5. The process for the isolation of Prol A comprising: (a) suspending blood serum in a nearly neutral buffered pH solution (b) centrifuging the resultant suspension at 6500 g to isolate a first supernatant (c) centrifuging the first supernatant at 6500 g to give a second supernatant (d) centrifuging the second supernatant at 27,000 g to give a third supernatant (e) centrifuging the third supernatant at $369 \times 10^3$ g at 0° C. to give a fourth supernatant (f) extracting the fourth supernatant with anhydrous ethyl ether and retaining the aqueous phase (g) heating the aqueous phase to 55° C.–60° C. and centrifuging at $40 \times 10^3$ g at 0° C. giving a fifth supernatant which is a clear, substantially colorless liquid (h) centrifuging the fifth supernatant liquid at $1.05 \times 10^5$ g at 0° C. yielding a sixth supernatant (i) extracting the sixth supernatant with anhydrous ethyl ether and retaining the aqueous phase (j) heating the aqueous phase to 55° C.–60° C. and centrifuging at $1.05 \times 10^5$ g at 0° C. yielding a seventh supernatant and (k) centrifuging the seventh supernatant at $369 \times 10^3$ g at 0° C. yielding Prol A as the sediment.

* * * * *